United States Patent
DiMauro et al.

(10) Patent No.: US 7,288,108 B2
(45) Date of Patent: Oct. 30, 2007

(54) RED LIGHT IMPLANT FOR TREATING PARKINSON'S DISEASE

(75) Inventors: Thomas M. DiMauro, Southboro, MA (US); Mohamed Attawia, Canton, MA (US); Chantal Holy, Somerville, MA (US); Sean Lilienfeld, Sharon, MA (US); Jeffrey K. Sutton, Medway, MA (US); Michael Ward, Providence, RI (US)

(73) Assignee: Codman & Shurtleff, Inc., Raynham, MA (US)

( * ) Notice: Subject to any disclaimer, the term of this patent is extended or adjusted under 35 U.S.C. 154(b) by 73 days.

(21) Appl. No.: 11/079,784

(22) Filed: Mar. 14, 2005

(65) Prior Publication Data

US 2006/0206172 A1 Sep. 14, 2006

(51) Int. Cl.
*A61N 5/06* (2006.01)
(52) U.S. Cl. .......................... 607/92; 128/898; 607/88
(58) Field of Classification Search ................ 128/898; 607/88–94
See application file for complete search history.

(56) References Cited

U.S. PATENT DOCUMENTS

| | | | |
|---|---|---|---|
| 5,445,608 A * | 8/1995 | Chen et al. | 604/20 |
| 5,707,396 A * | 1/1998 | Benabid | 607/2 |
| 6,537,304 B1 | 3/2003 | Oron | |
| 6,921,413 B2 * | 7/2005 | Mahadevan-Jansen et al. | 607/89 |
| 2002/0122621 A1 * | 9/2002 | Li | 385/31 |
| 2004/0073278 A1 | 4/2004 | Pachys | |
| 2004/0219600 A1 * | 11/2004 | Williams et al. | 435/7.1 |
| 2005/0175658 A1 | 8/2005 | DiMauro | |
| 2006/0004317 A1 | 1/2006 | Mauge | |
| 2006/0155348 A1 * | 7/2006 | deCharms | 607/89 |

FOREIGN PATENT DOCUMENTS

| | | |
|---|---|---|
| RU | 2200041 | 3/2003 |
| RU | 2222362 | 1/2004 |

OTHER PUBLICATIONS

Yaroslavsky, Optical Properties of Selected Native and Coagulated human Brain Tissue in vitro In The Visible and Near Infrared Spectral Range, Phys. Med. Biol., 2002, pp. 2059-2073, vol. 47.
Wong-Riley, Light-emitting diode treatment reverses the effect of TTX on cytochrome osidase in neurons, Neuroreport, Oct. 8, 2001, pp. 3033-3037, vol. 12(14).
Yamamoto, Involvement of the olfactory system in learning and memory: a close correlation between the olfactory deficit and the course of Alzheimer's disease?, Yakubutsu Seishin Kodo, 1991, pp. 223-235, vol. 11(4).
Yamamoto, Characteristics of memory dysfunction in olfactory bulbectomized rats and the effects of cholinergic drugs, Behav Brain Res, Feb. 1997, pp. 57-62, vol. 83(1-2).
Volotovskaia, Antioxidant action and therapeutic efficacy of laser irradiation blood in patients with ischemic heart disease, Vopr Kurortol Lech Fiz Kult, May-Jun. 2003, pp. 22-25, vol. 3.

(Continued)

*Primary Examiner*—Henry M Johnson, III

(57) ABSTRACT

This invention relates to an implantable device that delivers an effective amounts of red light to the substantia nigra as a treatment for Parkinson's Disease (PD).

14 Claims, 6 Drawing Sheets

OTHER PUBLICATIONS

Vladimirov, Molecular and cellular mechanisms of the low intensity laser radiation effect, Biofizika, Mar.-Apr. 2004, pp. 339-350, vol. 49(2).

Sohranji, Local and cortical effects of olfactory bulb lesions on trophic support and cholingeric function and their modulation by estrogen, J Neurobiol, Nov. 2000, pp. 61-74, vol. 45(2).

Tsuboi, Tau pathology in the olfactory bulb correlates with Braak stage, Lewy body pathology and apolipoprotein epsilon4, Neuropathol Appl Neurobiol., Oct. 2003, pp. 503-510, (5).

Powers, Light dosimetry in brain tissue: an in vivo model applicable to photodynamic therapy, Lasers Surg Med., 1986, pp. 318-322, vol. 6(3).

Qiu, Interleukin-6, beta-amyloid peptide and NMDA interactions in rat cortical neurons, J Neuroimmunol, 2003, pp. 51-57, vol. 139(1-2).

Romm, Action of laser radiation on the peroxide chemiluminescence of wound exudate, Biull Eksp Biol Med., Oct. 1986, pp. 426-428, vol. 102(10).

Mann, Alzheimer's disease: an olfactory connection?, Mech Ageing Dev., Jan. 1099, pp. 1-15, vol. 42(1).

Hozumi, Characteristics of changes in cholinergic function and impairment of learning and memory-related behavior induced by olfactory bulbectomy, Behav Brain Res., Jan. 2003,pp. 9-15, vol. 138(1).

Huell, Interleukin-6 is present in early stages of plaque formation and is restricted to the brains of Alzheimer's disease patients, Act Neuropathol (Bert), 1995, pp. 544-551, vol. 89(6).

Iakymenko, Regulatroy role of low-intensity laser radiation on the status of antioxidant system, Ukr. Biokhim Zh., Jan.-Feb. 2001, pp. 16-23, vol. 73(1).

Ji, Interstitial photoradiation injury of normal brain, Lasers Surg Med, 1992, pp. 425-431, vol. 12(4).

Kamanli, Plasma lipid peroxidation and antioxidant levels in patients with rheumatoid arthritis, Cell Biochem Funct., Jan.-Feb. 2004, pp. 53-57, vol. 22(1).

Klebanov, Effect of low intensity laser light in the red range on macrophages superoxide dismutase activity, Biofizika, May-Jun. 2003, pp. 462-473, vol. 48(3).

Konchugova, Immunodepressive effect of transcerebral lasers, Biull Eksp Biol Med., Apr. 1993, pp. 391-393, vol. 115(4).

Kovacs, beta-amyloid deposition and neurofibrillary tangle formation in the olfactory bulb in ageing and Alzheimer's disease, Neuropathol Appl Neurobiol., Dec. 1999, pp. 481-491, vol. 25(6).

Kovacs, Olfactory centres in Alzheimer's disease: olfactory bulb is involved in early Braak's stages, Neuroreport., Feb. 2001, pp. 285-288, vol. 12(2).

Chen, Effects of light beam size on fluence distribution and depth of necrosis in superficially applied photodynamic therapy of normal rat brain, Photochem Photobiol., Sep. 1992, pp. 379-384, vol. 56(3).

Cottrell, Mitochondrial enzyme-deficient hippocompal neurons and chorodial cells in AD., Neurology, Jul. 2001, pp. 260-264, vol. 57(2).

Cottrell, The role of cytochrome c oxidase deficient hippocampal neurons in Alzheimer's disease, Neuropathol Appl Neurobiol., Oct. 2002, pp. 390-396, vol. 28(5).

Davies, Axonal loss from the olfactory tracts in Alzheimer's disease, Neurobiol Aging., Jul.-Aug. 1993, pp. 353-357, vol. 14(4).

Del Bo, Reciprocal control of inflammatory cytokines, IL-1 and IL-6, and beta-amyloid production in cultures, Neurosci Lett., Mar. 1995, pp. 70-74, vol. 188(1).

Elias, Hyperthermia from interstitial laser irradiation in normal rat brain, Lasers Surg Med., 1987, pp. 370-375, vol. 7(4).

Giuliani, Very low level laser therapy attenuates edema and pain in experimental models, Int J Tissue React., 2004, pp. 29-37, vol. 26(1-2).

Gorbatenkova, Reactivation of superoxide dismutase by the helium-neon laser irradiation, Biofizika, Jul.-Aug. 1988, pp. 717-719, vol. 33(4).

Gorbatenkova, The red light of the helium-neon laser reactivates superoxide dismutase, Biull Eksp Biol Med., Mar. 1989, pp. 302-305, vol. 107(3).

Hass, Inducible nitric oxide synthase and argininosuccinate synthetase: co-induction in brain tissue of patients with Alzheimer's dementia and following stimulation with beta-amyloid 1-42 in vitro, Neurosci Lett., Apr. 5, 2002, pp. 121-125, vol. 322(2).

Hallam, An investigation of the effect of tacrine and physostigmine on spatial working memory deficits in the olfactory bulbectomised rat, Behav Brain Res., Aug. 31, 2004, pp. 481-486, vol. 153(2).

Balaban, He-Ne laser irradiation of single identified neurons, Lasers Surg Med, 1992, pp. 329-337, vol. 12(3).

Aleksandrova, Increased level of beta-amyloid in the brain of bulbectomized mice, Feb. 2004, pp. 176-180, vol. 69(2).

Aliev, Atherosclerotic lesions and mitochondria DNA deletions in brain microvessels as a central target for the development of human AD and AD-like pathology in aged transgenic mice, Ann N Y Acad Sci., Nov. 2002, pp. 45-64, vol. 977.

Anders, Low power laser irradiation alters the rate of regeneration of the rat facial nerve, Lasers Surg Med., 1993, pp. 72-82, vol. 13(1).

Wollman, In vitro cellular processes sprouting in cortex microexplants of adult rat brains induced by low power laser irradiation, Neurologic Research, Jul. 1998, pp. 470-472, vol. 20.

Wollman, Low power laser irradiation enhances migration and neurite sprouting of cultured rat embryonal brain cells, Neurological Research, Oct. 1996, pp. 467-470, vol. 18.

Snyder, Quantitation of Calcitonin Gene-Related Peptide mRNA and Neuronal Cell Death in Facial Motor Nuclei Following Axotomy and 633 nm Low Power Laser Treatment, Lasers in Surgery and Medicine, 2002, pp. 216-222, vol. 31.

Vladimirov, Photobiological Principles of Therapeutic Applications of Laser Radiation, Biochemistry, 2004, pp. 81-90, vol. 69(1).

Vladimirov, Photoreactivation of Superoxide Dismutase by Intensive Red (Laser) Light, Free Radical Biology & Medicine, 1998, pp. 281-286, vol. 5.

Schindl, Low-Intensity Laser Therapy: A Review, Journal of Investigative Medicine, Sep. 2000, pp. 312-326, vol. 48(5).

Neuman, Narrow-band red light phototherapy in perennial allergic rhinitis and nasal polyposis, Annals of Allergy, Asthma, & Immunology, Apr. 1997, pp. 399-406, vol. 78.

Mochizuki-Oda, Effects of near-infra-red laser irradiation on adenosine triphosphate and adenosine diphosphate contents of rat brain tissue, Neuroscience Letters, 2002, pp. 207-210, vol. 323.

Leung, Treatment of Experimentally Induced Transient Cerebral Ischemia With Low Energy Laser Inhibits Nitric Oxide Synthase Activity and Up-Regulates the Expression of Transforming Growth Factor-Beta 1, Lasers in Surgery and Medicine, 2002, pp. 283-288, vol. 31.

Hebeda, Light Propagation in the Brain Depends on Nerve Fiber Orientation Experimental Study, Neurosurgery, Oct. 1994, pp. 1992-1998, vol. 35(4).

Byrnes, Light Promotes Regeneration and Functional Recovery and Alters the Immune Response After Spinal Cord Injury, Lasers in Surgery and Medicine, 2005, pp. 1-15, vol. 9999.

Anders, Phototherapy promotes regeneration and functional recovery of injured peripheral nerve, Neurological Research, Mar. 2004, pp. 233-239, vol. 26.

Cho, Effect of low-level laser therapy on osteoarthroplasty in rabbut, In Vivo, Sep.-Oct. 2004, pp. 585-591, vol. 18(5).

Dugan, Fullerene-based antioxidants and neurodegenerative disorders, Parkin. Relat. Disord., 1002, Jul., pp. 243-246, vol. 7 (3).

Ebadi, Peroxynitrite and mitochondrial dysfunction in the pathogenesis of Parkinson's disease, Antioxidants & Redox Signaling, 2003, pp. 319-335, vol. 5(3).

Gonzalez, Protection against MPP+ neurotoxicity in cerebellar granule cells by antioxidants, Cell Biology Int'l, (2004) pp. 373-380, vol. 28.

Itoh, Defects of Cytochrome c Oxidase in the Substantial Nigra of Parkinson's Disease: An Immunohistochemical and Morphometric Study., Mov. Disord., Jan. 1997, pp. 9-16, vol. 12(1).

Karu, Suppression of Human Blood Chemiluminescence By Diode Laser Irradiation at Wavelengths 660, 820, 880 or 950 nm., Laser Ther. 1993, pp. 103-109, vol. 5.

Nakao, Overexpressing Cu/Zn superoxide dismutase enhances survival of transplanted neurons in a rat model of Parkinson's disease, Nat. Med. Mar. 1995, pp. 226-231 vol. (3).

Ostrakhovich, Active forms of oxygen and nitrogen in blood cells of patients with rheumatoid arthritis: effect of laser therapy, Vestn Ross Akad Med Nauk. 2001, pp. 23-27, vol. 5.

Vitreshchak, Laser Modification of the Blood in Vitro and in Vivo in Patients with Parkinson's Disease Bull. Exp. Biol. Med. May 2003 430-432, vol. 135(5).

Walicke, Purification of a human red blood cell protein supporting the survival of cultured CNS neurons and its identification as catalase, J. Neuroscience, Apr. 1986, pp. 1114-1121, vol. 6(4).

Wong-Riley, Photobiomodulation directly benefits primary neurons functionally inactivated by toxins: role of cytochrome c oxidase, J. Biol. Chem. Feb. 11, 2005, pp. 4761-4771, 280(6), Epub Nov. 22, 2004.

* cited by examiner

RED LIGHT IMPLANT FOR TREATING PARKINSON'S DISEASE

BACKGROUND OF THE INVENTION

Decreased neuronal energy production and increased oxidative stress are believed to be major components in the onset of Parkinson's Disease. It is believed that the substantia nigra contains high levels of iron, which helps catalyze oxygen to reactive oxygen species (ROS). The ROS then degrade dopamine-containing neurons. It is further believed that neurotoxins may be the cause of decreased neuronal energy output in the substantia nigra.

The literature describes the general use of anti-oxidants as potent neuroprotective agents for Parkinson's disease. For example, Dugan, *Parkin. Relat. Disord.,* 1002, July. 7, (3) 243–6, describes the use of fullerene-based antioxidants as neuroprotective drugs. In addition, oral administration of ascorbic acid has been tried as a therapy for Parkinson's Disease. To date, however, none of the therapies involving systemic administration of anti-oxidants has been shown to be successful. One possible reason for their failure was their inability to cross the blood brain barrier.

SUMMARY OF THE INVENTION

This invention relates to an implantable diode that emits red light onto the substantia nigra as a treatment for Parkinson's Disease (PD).

It has been reported in the literature that near infra-red light saves neurons that have been challenged by neurotoxics from apoptosis. In particular, Wong-Riley, *J. Biol. Chem.* 2004, e-pub November 22, reports that irradiating neurons with 670 nm red light significantly reduced neuronal cell death induced by 300 mM KCN from 83.6% to 43.5%.

The general concept of repairing brain cells through red light irradiation is also well supported by the literature. Wollman, *Neurol. Res.* 1998, July. 20(5) 470–2 reports that providing daily 3.6 J/cm$^2$ doses of red light from a He—Ne laser to cortex explants caused a significant amount of sprouting of cellular processes outgrowth. Wollman concludes that the irradiation induces neurite processes sprouting and improves nerve tissue recovery. Similarly, Wollman, *Neurol. Res.* 1996 October 18(5) 467–70 reports the enhanced migration and massive neurite sprouting of cultured rat embryonal brain cells subject to an 8 minute dose of a 0.3 mW, He—Ne laser. Therefore, the red light of the present invention may further cause repair and regeneration of damaged dopaminergic cells.

Therefore, in accordance with the present invention, there is provided a method of treating a patient having Parkinson's Disease, comprising the steps of:
  a) irradiating a portion of a substantia nigra of the patient with an effective amount of red light.

Also in accordance with the present invention, there is provided a method of treating a patient having Parkinson's disease, comprising the steps of:
  a) providing a fiber optic cable having a proximal end portion and a distal end portion;
  b) implanting the fiber optic cable into the patient's brain, and
  c) delivering red light through the fiber optic cable to irradiate a portion of a substantia nigra with an effective amount of red light.

Also in accordance with the present invention, there is provided a device for treating a patient having Parkinson's disease, comprising:
  a) a fiber optic cable having a proximal end portion and a distal end portion;
  b) an anchor attached to the proximal end portion of the fiber optic cable for fixing the fiber optic cable to the patient's skull.

Without wishing to be tied to a theory, it is believed that the therapeutic neuroprotective and neuroregenerative effects of red light described above may be due to a) an increase in adenosine triphosphate (ATP) production in the irradiated neurons, and b) an increase in the activity of local anti-oxidant enzymes superoxide dismutase (SOD) and catalase.

It is believed that irradiating neurons in the brain with red light will likely increase ATP production from those neurons. Mochizuki-Oda, *Neurosci. Lett.* 323 (2002) 208–210, examined the effect of red light on energy metabolism of the rat brain and found that irradiating neurons with 4.8 W/cm$^2$ of 830 nm red light increased ATP production in those neurons by about 19%.

Without wishing to be tied to a theory, it is further believed that the irradiation-induced increase in ATP production in neuronal cell may be due to an upregulation of cytochrome oxidase activity in those cells. Cytochrome oxidase (also known as complex IV) is a major photoacceptor in the human brain. According to Wong-Riley, *Neuroreport,* 12:3033–3037, 2001, in vivo, light close to and in the near-infrared range is primarily absorbed by only two compounds in the mammalian brain, cytochrome oxidase and hemoglobin. Cytochrome oxidase is an important energy-generating enzyme critical for the proper functioning of neurons. The level of energy metabolism in neurons is closely coupled to their functional ability, and cytochrome oxidase has proven to be a sensitive and reliable marker of neuronal activity. Nonetheless, there is some doubt of an association between defects in cytochrome c oxidase in the substantia nigra and Parkinson's Disease. Itoh, *Mov. Disord.* 1997, January 12(1) 9–16.

By increasing the energetic activity of cytochrome oxidase, the energy level associated with neuronal metabolism may be beneficially increased. Indeed, the literature reports that red light reverses the inhibitory effects of neurotoxins upon cytochrome oxidase activity, leading to increased energy metabolism in neurons functionally inactivated by toxins. Wong-Riley *Neuroreport* 12(14) 2001:3033–3037 Wong-Riley, *J. Biol. Chem.*,e,pub, Nov. 22, 2004.

According to Kamanli, *Cell Biochem. Func.* 2004, 22:53–57, catalase detoxifies hydrogen peroxide and converts lipid hydroperoxides into non-toxic alcohols, and is essential for the inhibition of inflammation related to the function of neutrophils.

Gonzalez, *Cell Biology Int'l,* 28(2004) 373–80, reports the effectiveness of catalase in enhancing the viability of PD cells in culture. In particular, Gonzalez reports that 50 U/ml catalase increased the in vitro viability of cerebellar granule cells exposed to MPP+ neurotoxin from about 50% to about 75%. Furthermore, it is believed that catalase is superior to the anti-oxidants recited in the prior art because it is not only an anti-oxidant, it is also neurotrophic towards CNS neurons. See Wallicke, *J. Neuroscience,* April 1986, 6(4), 1114–21.

Romm, *Biull. Eksp. Biol. Med.* 1986 October 102(10) 426–8 reports that laser irradiation of wounds results in a decreased chemiluminescence that is attributable to activation of catalase in the tissue fluid.

Therefore, it is believed that irradiating the substantia nigra with an effective amount of red light will therapeutically increase of the activity of catalase in the irradiated region, thereby attenuating the deleterious effect of hydrogen peroxide upon the dopamine neurons in the substantia nigra.

According to Kamanli, supra, SOD catalyses dismutation of the superoxide anion into hydrogen peroxide.

SOD has been shown to be neuroprotective in a rat model of Parkinson's disease. Nakao *Nat. Med.* 1995, Mar. 1, (3) 226–231, reports that the survival of grafted dopaminergic neurons in transgenic rats designed to overexpress Cu/Zn SOD was about four times higher than those in control rats, and there was also a similar increase in functional recovery.

Vitreshchak, *Bull. Exp. Biol. Med.* 135(5) May 2003 430–432, reports that He—Ne irradiation of blood from Parkinson's patients produced a normalization of their Cu—Zn SOD activity. This means that patients having lower than normal levels of SOD increased their SOD to near normal levels. This paper further reports a decrease in the severity of PD (from 72 to 58 points) in these patients.

The literature repeatedly reports that red light irradiation of inactivated SOD increases its activity. For example, Vladimirov, Biochemistry (Moscow) 69(1) 2004, 81–90 provides a review including the photoreactivation of Cu—Zn SOD under He—Ne laser. Karu, *Laser Ther.* 1993, 5, 103–9 reports that reactive oxygen species in human blood were found to be suppressed after laser diode illumination at 660 nm, 820 nm, 880 nm and 950 nm. This affect has been attributed by other authors to the activation of SOD or catalase. Volotovskaia *Vopr Kurortol Zizioter Lech Fiz Kult* 2003 May–June(3)22–5 reports that 632 nm He—Ne laser irradiation of blood has an anti-oxidant effect as shown by activation of SOD. Ostrakhovich Vestn Ross Akad Med Nauk. 2001(5) 23–7 reports that infrared pulse laser therapy of RA patients caused an increase in SOD activity. Gorbatenkova *Biofizika,* 1988 July–August 33(4) 717–9 reports that SOD that was inactivated by hydrogen peroxide was reactivated by a 450–680 nm red light laser. Vladimirov, *Free Rad. Biol. Med.* 1988, 5(5–6) 281–6 reports the inactivation of SOD by its incubation in a low pH 5.9 solution and its subsequent reactivation by helium-neon laser light. Catalase was found to be reactivated as well. Cho, *In Vivo,* 2004, September–October 18(5) 585–91 reports on the use of low level laser therapy (LLLT) to treat knee joints that have been induced with OA by injection of hydrogen peroxide. SOD was reported to increase about 40% in the OA group as compared to controls.

Therefore, it is believed that irradiating the substantia nigra with an effective amount of red light will therapeutically increase of the activity of SOD in the irradiated region, thereby attenuating the deleterious effect of superoxide anion upon the dopamine neurons in the substantia nigra.

Since infrared light is known to induce molecular vibrations (the basis of infrared spectroscopy), one could easily theorize that the use of JR light, particularly higher energy JR (e.g. shorter wavelengths 600–900 nm) could induce vibrations in the enzymes (proteins) of interest (such as catalase or SOD). It may be that the activity of these enzymes is inhibited or inactivated by weak intermolecular attractions, such as hydrogen bonding, Van der Waals forces, or ion chelation, causing sub-optimal protein conformations, and that the introduction of red light energy causes molecular vibrations sufficient to disrupt these weak forces, thereby allowing the enzyme to return to it's active 3-D conformation upon relaxation. If such a mechanism of action was accurate, the adjunctive use of solutions to create slight changes in the local environment (pH, ionic strength, solvation) during the treatment could have profound effects upon the treatment, e.g. synergistic.

According to Leung, *Laser Surg. Med.* 31:283–288 (2002), nitric oxide enhances oxidative insult by reacting with superoxide anion to form a stronger oxidant, peroxynitrite, which leads to mitochondrial dysfunction, DNA damage and apoptosis. As a result, excess NO has been implicated as a contributing factor to dopaminergic cell loss causing Parkinson's disease. Ebadi, *Antioxidants & Redox Signaling,* 5(3), 2003, pp. 319–335.

Leung, supra, investigated the effect of low energy red laser after stroke in rats, and found that red light can both suppress NO synthase activity (and upregulate the expression of TGF-β1). In particular, Leung found that irradiating a portion of the rat's brain with a 660 nm red light (average power 8.8 mW, 2.64 J/cm$^2$) reduced NOS activity up to about 80% over that in unirradiated stroke rats, and up to about 60% over the NOS activity in normal rats. Leung concluded that the main findings of the study was that low energy laser may be protective by suppressing the activity of NOS and upregulating the expression of TGF-β1 in cerebral ischemia and reperfusion.

Without wishing to be theory, it is believed that irradiation of the substantia nigra portion of a Parkinson's brain will similarly therapeutically suppress NO synthase activity, thereby attenuating peroxynitrite activity.

DETAILED DESCRIPTION OF THE INVENTION

Figure 1:
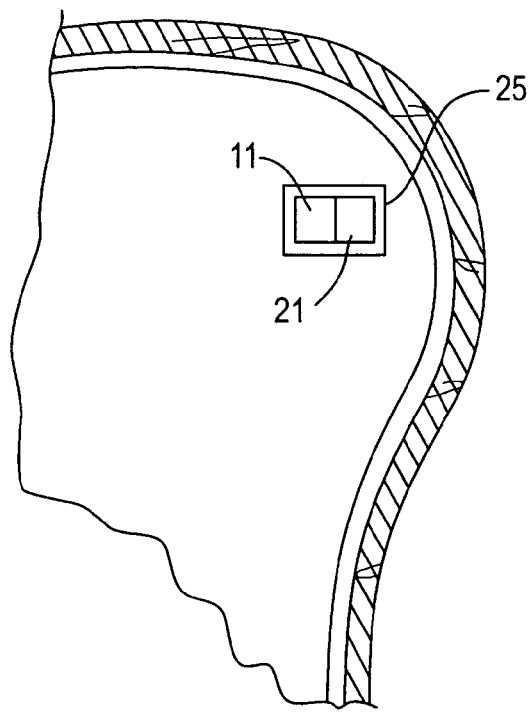
FIG. 1 is a cross-section of an LED implant of the present invention implanted within the brain of a patient having Parkinson's Disease.

Preferably, the red light of the present invention has a wavelength of between about 650 nm and about 1000 nm. In some embodiments, the wavelength of light is between 800 and 900 nm, more preferably between 825 nm and 835 nm. In this range, red light has not only a large penetration depth (thereby facilitating its transfer to the fiber optic and SN), but Wong-Riley reports that cytochrome oxidase activity is significantly increased at 830 nm, and Mochizuki-Oda reported increased ATP production via a 830 nm laser.

In some embodiments, the wavelength of light is between 600 and 700 nm. In this range, Wong-Riley reports that cytochrome oxidase activity was significantly increased at 670 nm. Wollman reports neuroregenerative effects with a 632 nm He—Ne laser.

In some embodiments, the light source is situated to irradiate adjacent tissue with between about 0.02 J/cm$^2$ and 200 J/cm$^2$ energy. Without wishing to be tied to a theory, it is believed that light transmission in this energy range will be sufficient to increase the activity of the cytochrome oxidase and anti-oxidant activity around and in the substantia nigra. In some embodiments, the light source is situated to irradiate adjacent tissue with between about 0.2 J/cm$^2$ and 50 J/cm$^2$ energy, more preferably between about 1 J/cm$^2$ and 10 J/cm$^2$ energy.

In some embodiments, the light source is situated to produce an energy intensity of between 0.1 watts/cm$^2$ and 10 watts/cm$^2$. In some embodiments, the light source is situated to produce about 1 milliwatt/cm$^2$.

Of note, it has been reported that the neuroprotective effects of red light can be effected by a single irradiation on the order of minutes. Wong-Riley, *J. Biol. Chem.* 2004, e-pub November 22, reports that irradiating neurons with 670 nm red light for only ten minutes results in neuroprotection. Similarly, Wong-Riley *Neuroreport* 12(14) 2001: 3033–3037 reports that a mere 80 second dose of red light irradiation of neuron provided sustained levels of cytochrome oxidase activity in those neurons over a 24 hour period. Wong-Riley hypothesizes that this phenomenon occurs because "a cascade of events must have been initiated by the high initial absorption of light by the enzyme".

Therefore, in some embodiments of the present invention, the therapeutic dose of red light is provided on approximately a daily basis, preferably no more than 3 times a day, more preferably no more than twice a day, more preferably once a day.

In some embodiments, the red light irradiation is delivered in a continuous manner. In others, the red light irradiation is pulsed in order to reduce the heat associated with the irradiation. Without wishing to be tied to a theory, it is believed that pulsed light may be more effective in achieving the vibratory oscillation of the catalase and SOD molecules.

In some embodiments, red light is combined with polychrome visible or white light Thus, there may be a substantial benefit to providing a local radiation of the substantia nigra with red laser light. The red light can be administered in a number of ways:
1) By implanting near the skull an implant having a red light LED, an antenna and a thin fiber optic terminating at the substantia nigra, and telemetrically powering the LED via an external antenna to deliver red light through the fiber optic to the substantia nigra.
2) By placing a fiber optic having a proximal light collector at the interior rim of the skull and running it to the substantia nigra, and then irradiating the proximal end via an external red light source. Red light can penetrate tissue up to about one cm, so it might be able to cross the skull and be collected by the collector.
3) By implanting a red light LED in the skull, and powering the LED via an internal battery.

In each case, there is produced an effective amount of local red or infrared irradiation around the substantia nigra. This light would then increase local ATP production, and enhance SOD and catalase activity, thereby increasing the metabolism in and reducing the oxidative stress upon the substantia nigra.

Now referring to FIG. 1, there is provided an implant for treating Parkinson's disease comprising:
a) a Red Light emitting diode (LED) 11, and
b) an antenna 21 in electrical connection with the LED.

In use, the surgeon implants the device into the brain of the patient so that the device is adjacent to a portion of the substantia nigra. The Red light produced by the implant will then irradiate that portion of the substantia nigra.

In order to protect the active elements of the device from cerebrospinal fluid ("CSF"), in some embodiments, and again referring to FIG. 1, the Red light LED is encased in a casing 25. This casing both protects the LED components from the CSF, and also prevents the LED components from eliciting a violent immune reaction In some embodiments, the casing is made of a Red light transparent material. The Red light transparent material may be placed adjacent the LED component so that Red Light may be easily transmitted therethrough. In some embodiments, the transparent casing is selected from the group consisting of silica, alumina and sapphire. In some embodiments, the light transmissible material is selected from the group consisting of a ceramic and a polymer. Suitable red light-transmissible ceramics include alumina, silica, CaF, titania and single crystal-sapphire. Suitable light transmissible polymers are preferably selected from the group consisting of polypropylene and polyesters.

In some embodiments, it may be desirable to locate the light emitting portion of the implant at a location separate from the LED, and provide a light communication means between the two sites. The light communication means may include any of a fiber optic cable, a wave guide, a hollow tube, a liquid filled tube, and a light pipe.

Figure 2:
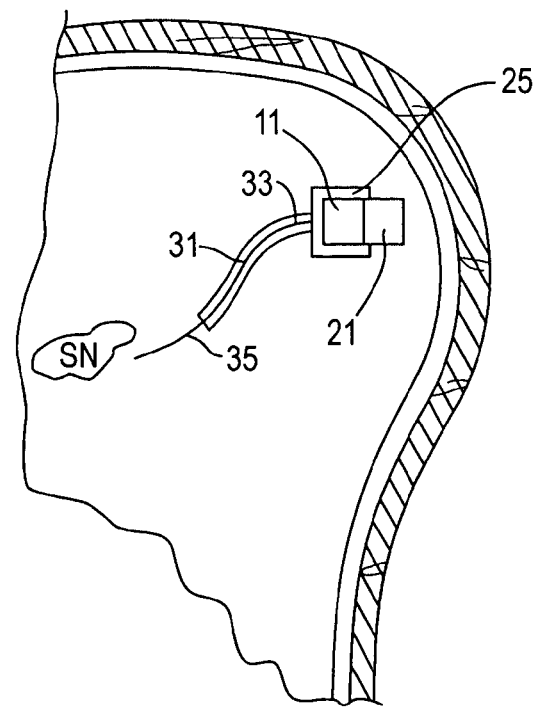
FIG. 2 is a cross-section of an implant of the present invention having a fiber optic cable and implanted within the brain of a patient having Parkinson's Disease.

Now referring to FIG. 2, there is provided an implant 1 for treating Parkinson's disease comprising:
a) a Red Light emitting diode (LED) 11,
b) an antenna 21 in electrical connection with the LED, and
c) a fiber optic cable 31 adapted to transmit Red light, the cable having a proximal end 33 connected to the LED an and a distal end portion 35.

Such a configuration would allow the distal end of the fiber optic to be located deep within the patient's brain near the substantia nigra and yet have the light source and associated components located near or in the skull in a less sensitive region. This configuration allows easier access to the light/controller should the need arise for service or maintenance, and also allow for more efficient transdermal energy transmission. Moreover, by using a hollow tube with reflective internal surfaces, light and therapeutic fluids (such as a fibroblast graft) could be delivered to the implanted device. The light source/controller implanted near the patient's skull could also be a simple, hollow chamber made to facilitate the percutaneous access described above. The advantages and benefits of this system include:
a) further removal from the deep site of the functional implant, thereby reducing risk of contamination of the deeper site by percutaneous access;
b) easier precutaneous access by being closer to the skin surface and having a larger surface area or target to access with the needle;
c) a larger volume could hold more therapeutic fluid to provide a longer duration of activity.

In use, the surgeon implants the device into the brain of the patient so that the antenna is adjacent the cranium bone and the distal end of the fiber optic cable is adjacent to the substantia nigral region of the brain.

In some embodiments, the proximal end portion of the fiber optic cable is provided with a cladding layer 41 of reflective material to insure that Red light does not escape the cable into untargeted regions of brain tissue.

Figure 3:
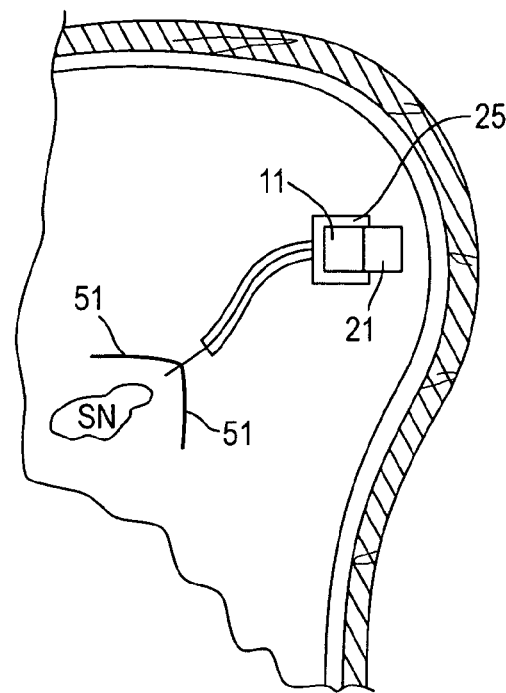
FIG. 3 is a cross-section of an implant of the present invention having a tyned fiber optic cable and implanted within the brain of a patient having Parkinson's Disease.

In some embodiments, the distal end portion of the fiber optic cable includes a plurality of fiber optic tynes 51 extending from the cable (as shown in FIG. 3). Since each of these tynes transmits Red light into brain tissue, the provision of tynes increases the volume of brain tissue that can be irradiated.

In some embodiments, the tynes located at distal end portion of the fiber optic cable are placed around the substantia nigra.

Figure 4A:
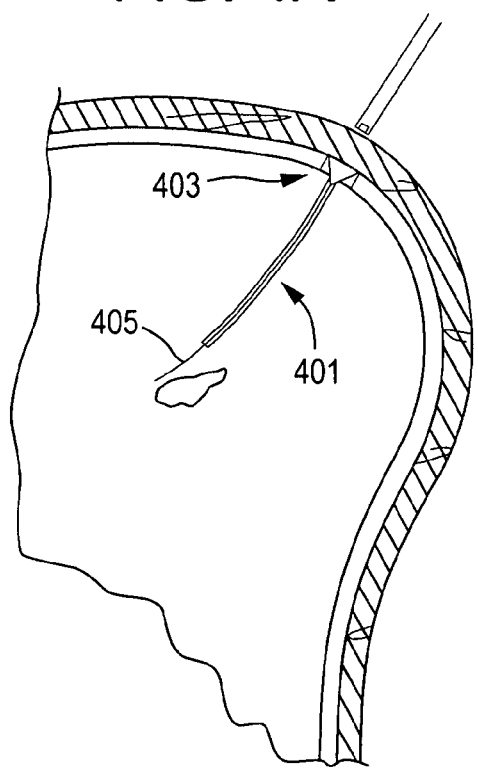
FIGS. 4A–4B are cross-sections of a fiber optic implant of the present invention implanted within the brain of a patient having Parkinson's Disease.
Figure 4B:
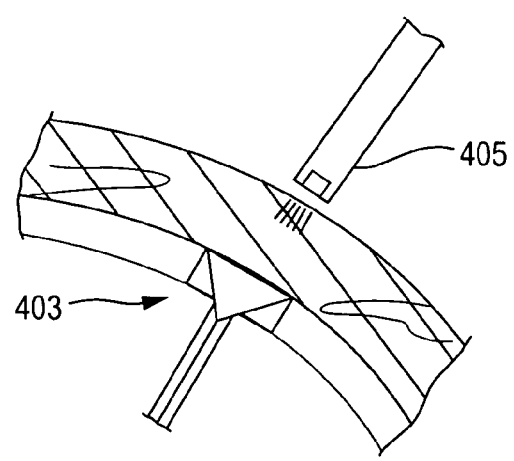

Because long wavelength red light can penetrate up to many centimeters, it might be advantageous to transcutaneously deliver the light the fiber optic. Now referring to FIGS. 4a–4c, in one embodiment, a fiber optic 401 having a proximal light collector 403 is placed at the interior rim of the skull and the distal end portion 405 of the cable (which is unclad) is run to the substantia nigra. Red light can then be delivered transcutaneously from a probe 415 to the collector 403, which will then transport the light to the substantia nigra.

Figure 4C:
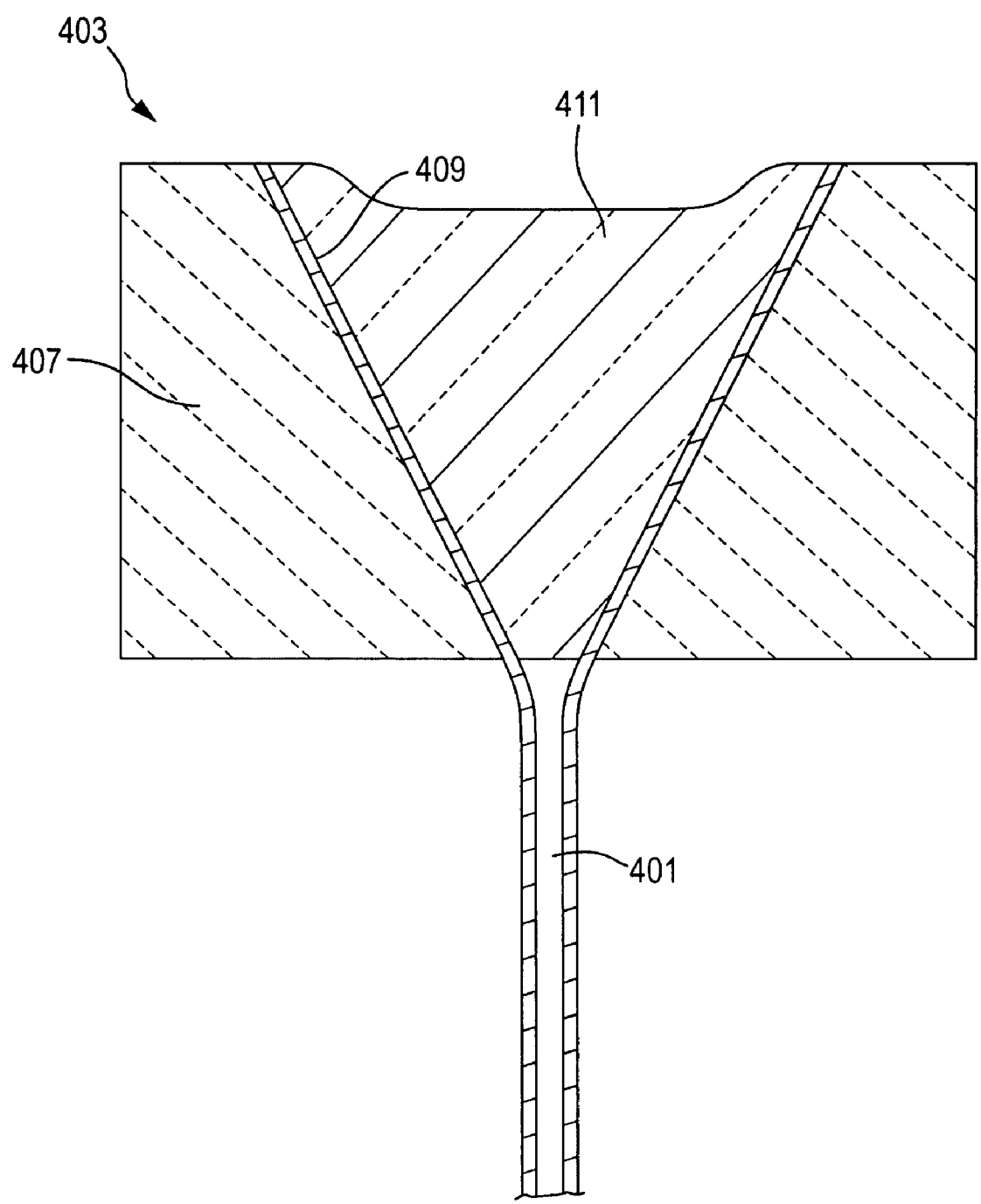
FIG. 4C is a cross-section of a fiber optic implant of the present invention.

In some embodiments, as in FIG. 4c, the collector 403 has a porous osteoconductive collar 407 for intergrating with the bone in the skull. The collector may comprise a funnel-shaped mirror 409 (made of titanium) that connects to the fiber optic cable 401 and is filed with a red light-transparent material 411 such as silica.

To enhance the propagation of light emitted from the end of the fiber, a lens could be placed at the distal end of the fiber to spread the light, or a diffuser such as a small sheet or plate of optical material could be used to create more surface area. Alternatively, one could create a series of lateral diffusers, such as grooves or ridges, along the distal portion of end of the fiber to spread light out from 360 degrees perpendicular to the axis of the fiber, as well as emanating directly out from the end of the fiber.

Figure 5:
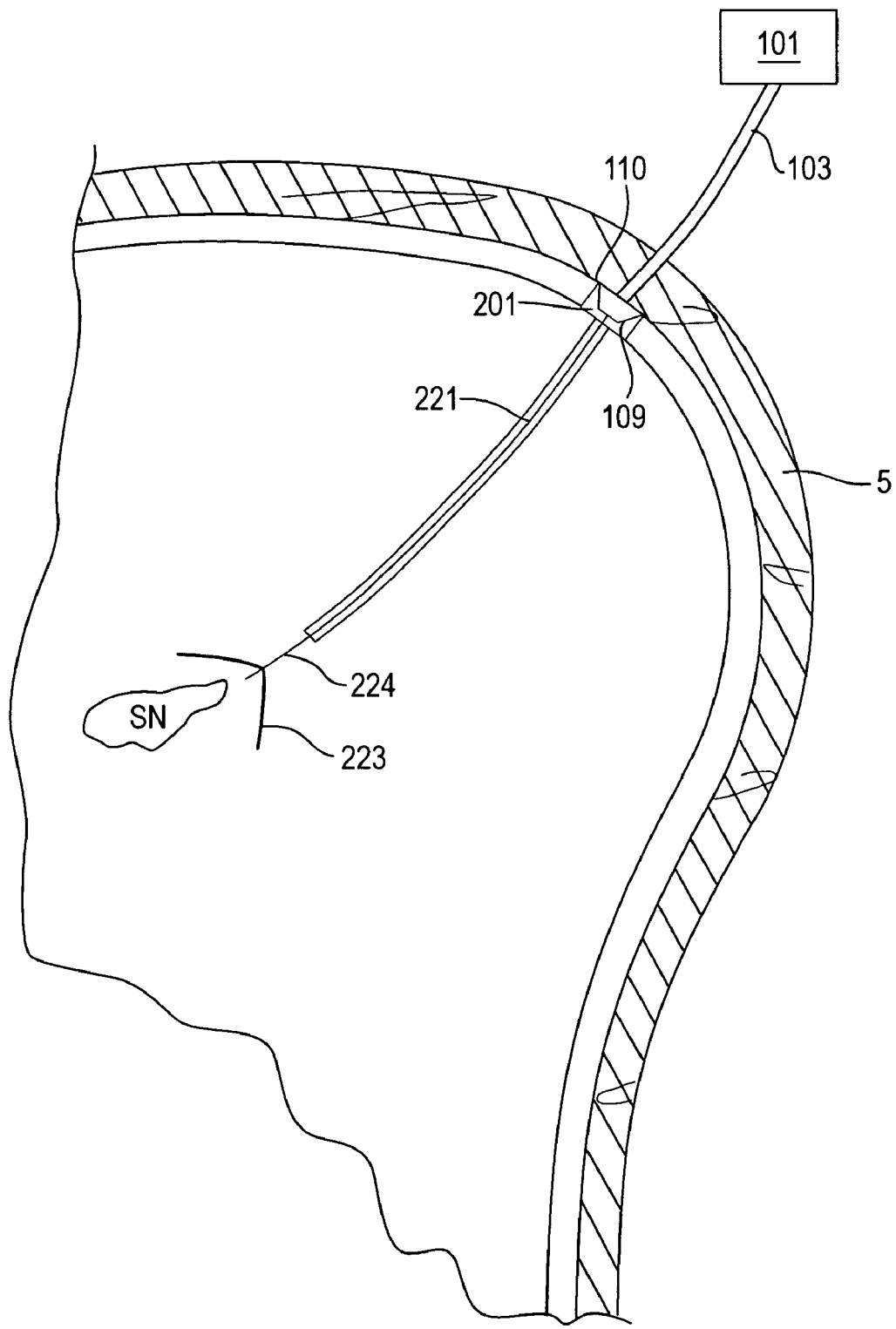
FIG. 5 is a cross-section of an implanted fiber optic implant irradiated by a light source.

Now referring to FIG. 5, there is provided an implant having an external light source. The externally based-control device has a light source 101 for generating light within the device. The light generated by this source is transmitted through fiber optic cable 103 through the patient's skin S to an internally-based light port 109 provided on the proximal surface 110 of the implant 201. The light port is adapted to be in light-communication with fiber optic cable 221 disposed upon the distal surface 203 surface of the implant. The tynes 223 disposed upon the distal portion 224 of the fiber optic cable receive the light and transmit the light to the adjacent brain tissue.

Figure 6:
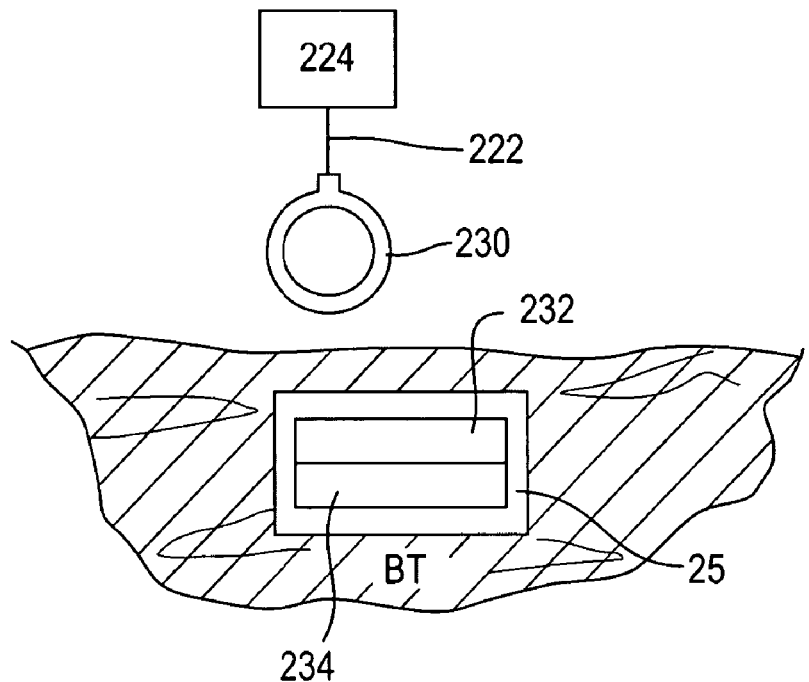
FIG. 6 is a cross-section of an Rf source energized an LED implant of the present invention.

Now referring to FIG. 6, there is provided an exemplary Red light unit having an internal light source. Externally based-control device 222 has an RF energy source 224 and an antenna 230 for transmitting signals to an internally-based antenna 232 provided on the prosthesis. These antennae 230, 232 may be electro-magnetically coupled to each other. The internal antenna 232 sends electrical power to a light emitting diode (LED) 234 disposed internally on the implant in response to the transmitted signal transmitted by the external antenna 230. The light generated by the LED travels across light transparent casing 25 and into the brain tissue BT.

Figure 7:
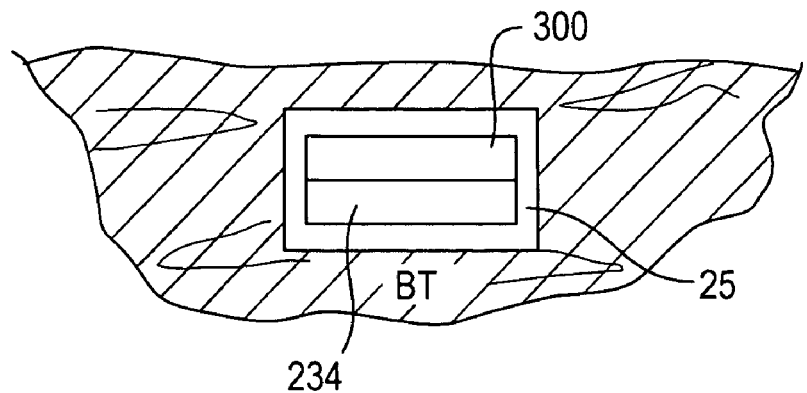
FIG. 7 is a cross-section of an LED implant of the present invention.

In some embodiments, and now referring to FIG. 7, the prosthesis having an internal light source further contains an internal power source 300, such as a battery (which could be re-chargeable), which is controlled by an internal receiver and has sufficient energy stored therein to deliver electrical power to the light source 234 in an amount sufficient to cause the desired light output.

When the implant is coupled with external energy, power can be transmitted into the internal device to re-charge the battery.

In some embodiments, the light generated by the implant is powered by wireless telemetry integrated onto or into the implant itself. In the FIG. 6 embodiment, the LED 234 may comprise a radiofrequency-to-DC converter and modulator. When radiofrequency signals are emitted by the external antenna 230 and picked up by the internal antenna 232, these signals are then converted by the receiver (not shown) into electrical current to activate the light source of the unit.

In one embodiment, the implant may have an internal processor adapted to intermittently activate the LED.

In some embodiments, the telemetry portion of the device is provided by conventional, commercially-available components. For example, the externally-based power control device can be any conventional transmitter, preferably capable of transmitting at least about 40 milliwatts of energy to the internally-based antenna. Examples of such commercially available transmitters include those available from Microstrain, Inc. Burlington, Vt. Likewise, the internally-based power antenna can be any conventional antenna capable of producing at least about 40 milliwatts of energy in response to coupling with the externally-generated Rf signal. Examples of such commercially available antennae include those used in the Microstrain Strainlink™ device. Conventional transmitter-receiver telemetry is capable of transmitting up to about 500 milliwatts of energy to the internally-based antenna.

Figure 8:
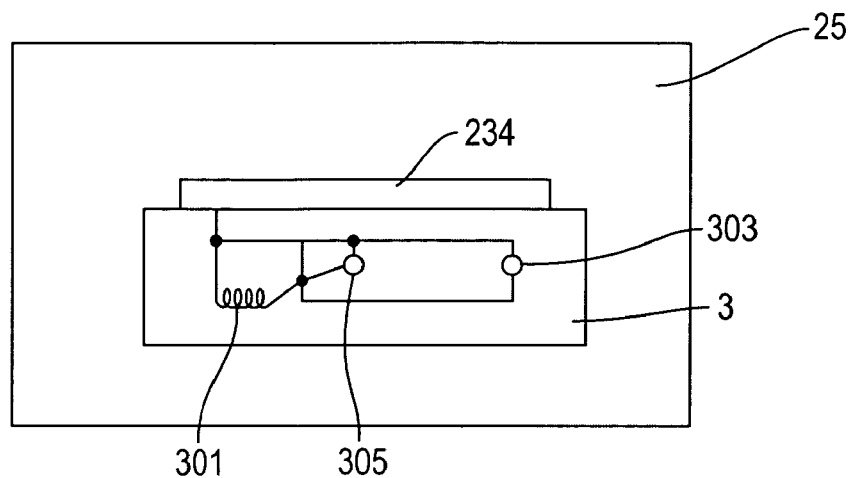
FIG. 8 is a schematic of electronics associated with an LED implant of the present invention.

In some embodiments, and now referring to FIG. 8, the implant includes a light emitting diode (LED) 234 built upon a base portion 3 of the implant, along with the required components to achieve trans-dermal activation and powering of the device. These components can include, but are not limited to, RF coils 301, control circuitry 303, a battery 305, and a capacitor. Such a device could be capable of intermittent or sustained activation without penetrating the skin, thereby avoiding trauma to the patient and/or risk of infection from skin-borne bacteria. As shown above, the accessory items needed to power and control the LED may be embedded within the implant. However, they could also be located on the surface(s) of the implant, or at a site adjacent to or near the implant, and in communication with the implant.

In some embodiments, the light source is provided on the implant and is adapted to be permanently implanted into the patient. The advantage of the internal light source is that there is no need for further transcutaneous invasion of the patient. Rather, the internally-disposed light source is activated by either a battery disposed on the implant, or by telemetry, or both. In some embodiments of the present invention using an internal light source, the light source is provided by a bioMEMs component.

Figure 9:
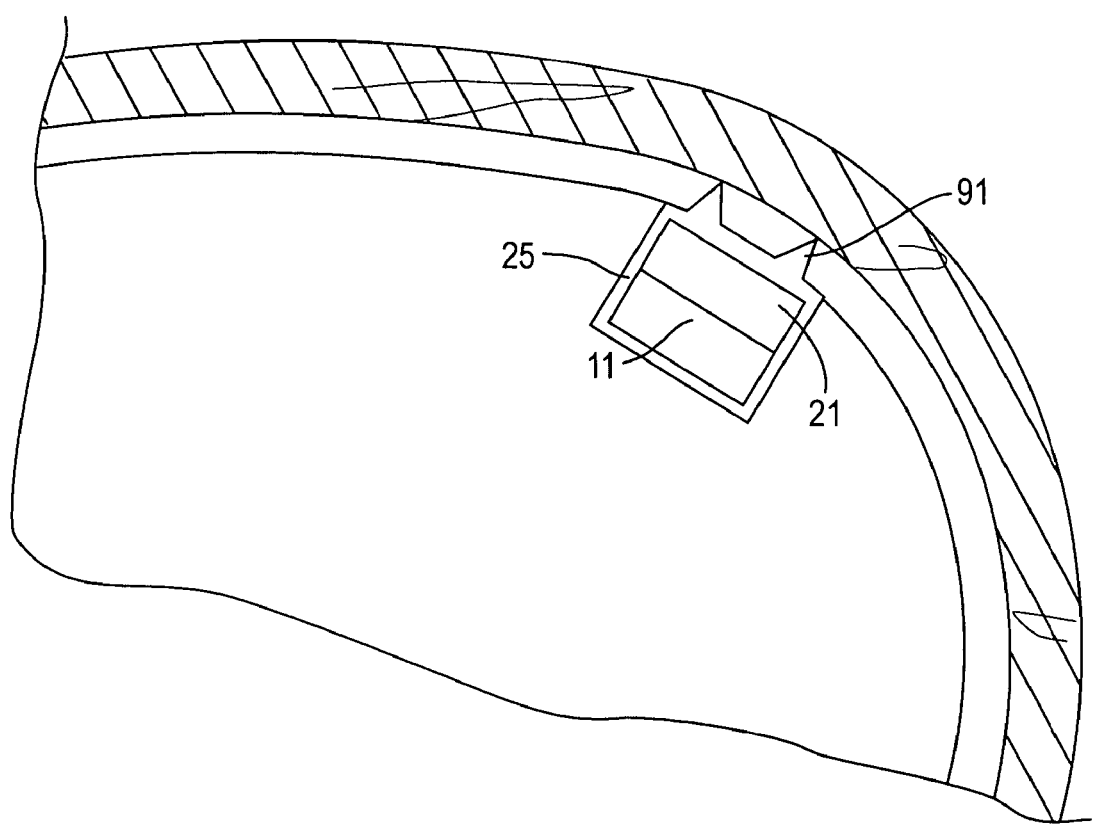
FIG. 9 is a cross-section of a toothed LED implant of the present invention implanted within the brain of a patient having Parkinson's Disease.

Because use of the present invention may require its repeated activation by Rf energy, it would be helpful if the user could be guaranteed that the implant remained in the same place within the skull. Accordingly, in some embodiments, and now referring to FIG. 9, the device of the present invention comprises anchors 91, preferably projecting from the casing 25. Preferably, the anchors are placed on the proximal side of the device, adjacent the antenna 21. In this position, the anchor may be inserted into the bone of the skull S, thereby insuring its position.

It is anticipated that the present invention would be useful in treating neurodegenerative diseases such as Parkinson's Disease, SRO Syndrome, progressive Supernuclear Palsy, parkinsonism and Alzheimer's Disease.

It is anticipated that functional benefits following red light irradiation are site-specific. In some embodiments, the fiber optic is placed to irradiate the dorsal striatum; the lateral striatum; the caudate nucleus; the putamen; the posterior putamen; the anterior putamen/caudate nucleus complex.

In some embodiments, the fiber optic is placed to irradiate the substantia nigra. Therefore, the fiber optic may be placed within about an 4 mm of the substantia nigra. The surgeon may access the substantia nigra though the brain parenchyma using stereotactic MRI guidance. As it is desirable to use a flexible material as the fiber optic in order to reduce migration, the distal end of the fiber optic may be placed near the substantia nigra with the help of a relatively stiff introducer cannula.

In some embodiments, the patient can receive a unilateral fiber optic, while in other the patient can receive bilateral fiber optic. In some embodiments, a plurality of cables is used to deliver light to each target region.

In some embodiments, a red light source or red light collector and the proximal end of the fiber optic are placed in the chest. This allows the surgeon to conduct maintenance activity on an implanted light source without having to re-open the cranium. In addition, location within the chest also lessens the chances of surface erosion.

In some embodiments, electrical stimulation of a portion of the brain (other than the substantia nigra) is carried out. In some embodiments, the stimulation is accomplished with a separate conductive wire. In others, the stimulation is in part accomplished by painting a conductive strip upon a longitudinal surface of the fiber optic cable.

We claim:

1. A method of treating a patient having Parkinson's disease, comprising the steps of:
   a) providing a fiber optic cable having a proximal end portion and a distal end portion;
   b) implanting the fiber optic cable into the patient's brain, and
   c) delivering light through the fiber optic cable to irradiate a portion of a substantia nigra with an effective amount of light, wherein the light is continuous and has a wavelength of between about 600 nm and about 900 nm and wherein the light is transcutaneously delivered to the fiber optic cable from a light source located outside the patient.

2. The method of claim 1 wherein the proximal end portion of the fiber optic cable is located within the patient's skull.

3. The method of claim 1 wherein the proximal end portion of the fiber optic cable is located within the patient's chest.

4. The method of claim 1 wherein the distal end portion of the fiber optic is located within about 1 inch of the substantia nigra.

5. The method of claim 1 wherein the light irradiates at least two portions of the substantia nigra.

6. The method of claim 1 wherein the implantation of the fiber optic cable is accomplished through a cannulated introducer.

7. The method of claim 1 wherein the distal end portion of the fiber optic cable is adapted to diffuse the light.

8. A device for treating a patient having Parkinson's disease, comprising:
   a) a fiber optic cable having a proximal end portion and a distal end portion;
   b) an anchor attached to the proximal end portion of the fiber optic cable for fixing the fiber optic cable to the patient's skull, wherein the anchor comprises a porous collar.

9. The device of claim 8 wherein the distal end portion of the fiber optic cable is adapted to diffuse light.

10. The device of claim 9 wherein the distal end portion of the fiber optic cable comprises a lens.

11. The device of claim 9 wherein the distal end portion of the fiber optic cable comprises a plurality of lateral diffusers.

12. The device of claim 8 wherein the porous collar defines an inner surface, and wherein the anchor further comprises light reflective material located upon a portion of the inner surface.

13. The device of claim 12 wherein the inner surface defines a frustocone having a distal end portion.

14. The device of claim 13 wherein the proximal end portion of the fiber optic cable is connected to the distal end portion of the frustocone.

* * * * *